US011013521B2

(12) United States Patent
Jaramaz et al.

(10) Patent No.: US 11,013,521 B2
(45) Date of Patent: May 25, 2021

(54) HYBRID CONTROL OF A CUTTING TOOL (71) Applicant: Blue Belt Technologies, Inc., Pittsburgh, PA (US)

(72) Inventors: Branislav Jaramaz, Pittsburgh, PA (US); Gary David Carlson, Jr., Pittsburgh, PA (US); Samuel Clayton Dumpe, Beaver, PA (US)

(73) Assignee: Blue Belt Technologies, Inc., Pittsburgh, PA (US)

(*) Notice: Subject to any disclaimer, the term of this patent is extended or adjusted under 35 U.S.C. 154(b) by 0 days.

(21) Appl. No.: 16/345,516

(22) PCT Filed: Oct. 27, 2017

(86) PCT No.: PCT/US2017/058777
§ 371 (c)(1),
(2) Date: Apr. 26, 2019

(87) PCT Pub. No.: WO2018/081571
PCT Pub. Date: May 3, 2018

(65) Prior Publication Data
US 2019/0307470 A1  Oct. 10, 2019

Related U.S. Application Data (60) Provisional application No. 62/414,490, filed on Oct. 28, 2016.

(51) Int. Cl.
A61B 17/17 (2006.01)
A61B 34/20 (2016.01)
(Continued)

(52) U.S. Cl.
CPC ...... *A61B 17/1764* (2013.01); *A61B 17/1626* (2013.01); *A61B 17/1675* (2013.01);
(Continued)

(58) Field of Classification Search
None
See application file for complete search history.

(56) References Cited

U.S. PATENT DOCUMENTS 5,613,970 A    3/1997  Houston et al.
6,757,582 B2   6/2004  Brisson et al.
(Continued)

OTHER PUBLICATIONS

International Search Report and Written Opinion for PCT/US2017/058777 dated Feb. 8, 2018.

*Primary Examiner* — Samuel S Hanna
(74) *Attorney, Agent, or Firm* — Troutman Pepper Hamilton Sanders LLP (57) ABSTRACT A system for preparing a bone for receiving an implant is described. The system includes a cutting tool and a cutting guide. The cutting tool includes a cut guard configured to sheath at least a portion of a cutting surface of the cutting tool, and an engagement portion. The cutting guide includes a baseplate configured to be positioned onto the bone and a cut guide portion removably attached to the baseplate. The cut guide portion includes a cutting channel, the cutting channel being sized and shaped to receive the engagement portion of the cut guard and guide the cutting tool to cut a receiving channel into the bone, wherein the receiving channel includes a depth profile matching an implant to be inserted into the receiving channel.

4 Claims, 8 Drawing Sheets (51) Int. Cl.
*A61B 17/16* (2006.01)
*A61B 17/32* (2006.01)

(52) U.S. Cl.
CPC .............. *A61B 17/32* (2013.01); *A61B 34/20* (2016.02); *A61B 2017/320052* (2013.01)

(56) References Cited

U.S. PATENT DOCUMENTS

| | | | |
|---|---|---|---|
| 2007/0219559 A1* | 9/2007 | Heavener | A61B 17/1764 606/87 |
| 2011/0029091 A1* | 2/2011 | Bojarski | A61F 2/30942 623/20.32 |
| 2011/0106093 A1 | 5/2011 | Romano et al. | |
| 2011/0262224 A1 | 10/2011 | McCandless et al. | |
| 2013/0116698 A1* | 5/2013 | Wilkinson | A61B 17/157 606/88 |
| 2013/0165936 A1 | 6/2013 | Myers | |

* cited by examiner

SECTION A-A    FIG. 3C

HYBRID CONTROL OF A CUTTING TOOL

CLAIM OF PRIORITY

This application is a U.S. national stage filing under 35 U.S.C. § 371 of International PCT Application No. PCT/US2017/058777, filed Oct. 27, 2017, which claims the benefit of priority to U.S. Provisional Application No. 62/414,490, titled "Hybrid Control of a Cutting Tool," filed Oct. 28, 2016, each of which is incorporated herein by reference in its entirety.

TECHNICAL FIELD

The present disclosure relates generally to controlling a navigated freehand surgical tool. More specifically, the present invention relates to a cut guide for mechanically constraining at least a portion of the cutting path of the tool.

BACKGROUND

In a total knee replacement surgery, a surgeon can place a first implant in the distal end of the patient's femur and a second implant in the proximal end of the tibia. For optimal fit, the surgeon must use a cutting tool to shape each of these bones so that they can receive their respective implants with as little gap as possible. If too much bone is removed, the implant may not fit properly or be loose, which can result in implant dislocation or failure.

A common type of cutting element used for bone shaping is a spinning bur as is used by the hand-held robotically-assisted tool called the NAVIO®. NAVIO is a registered trademark of BLUE BELT TECHNOLOGIES, INC. of Pittsburgh, Pa. When this tool, which is optically tracked, is moved over a volume of bone that is to be removed, the system controls cutting action of its cutting element based on its position relative to the bone and the surgical plan, in one of two ways: control of the exposure of the cutting element and control of its speed. In a real-time feedback loop, the position tracking system reports the position of both the cutting element and the bone to the computer. These positions are compared to the surgical plan and the computer decides, in that moment, cutting should be allowed and communicates that decision to the tool. The user can move the tool freely over the target area and only the bone planned for removal will be removed, resulting in the preparation of the bone in a manner consistent with the surgical plan.

Sometimes, however, the cutting tool used by the surgeon is not ideally suited for all of the types of cuts that must be made. In addition to shaving portions off the outside of the bone, sometimes, for example, a channel must be cut into the bone and that channel may need to be at an angle that is not perpendicular to the face of the bone or which has a varying depth to properly receive the implant. While a spinning bur can make these types of cuts, they are very time-consuming to get the correct angle and depth, which makes it inefficient and results in a greater chance of infection.

SUMMARY

There is provided a device for use during an implant surgery. The device includes a baseplate configured to be positioned onto a first bone to be cut and a cut guide portion removably attached to the baseplate. The cut guide portion includes a cutting channel. The cutting channel is sized and shaped to receive at least a portion of a cutting tool and guide the cutting tool to cut a receiving channel in the first bone to be cut, wherein the receiving channel comprises a depth profile matching an implant to be inserted into the receiving channel.

In some embodiments, the baseplate may further comprise at least one engagement feature configured to mate with at least one receptacle on the first bone to be cut, thereby positioning the baseplate on the bone to be cut.

In some embodiments, the cutting channel may comprise an internal shape configured to fit the at least a portion of the cutting tool.

In some embodiments, the baseplate may be sized based upon the implant to be inserted into the receiving channel.

In some embodiments, the cut guide portion may be sized to provide a receiving channel for a plurality of implant sizes.

In some embodiments, the first bone to be cut may comprise a tibia.

In some embodiments, the baseplate may be configured to fit the first bone to be cut when a first side of the baseplate is positioned up and fit a second bone to be cut when a second side of the baseplate is positioned up.

There is also provided a system for preparing a bone for receiving an implant. The system includes a cutting tool and a cutting guide. The cutting tool comprises a cut guard configured to sheath at least a portion of a cutting surface of the cutting tool, and an engagement portion. The cutting guide comprises a baseplate configured to be positioned onto the bone and a cut guide portion removably attached to the baseplate. The cut guide portion comprises a cutting channel, the cutting channel being sized and shaped to receive the engagement portion of the cut guard and guide the cutting tool to cut a receiving channel into the bone, wherein the receiving channel comprises a depth profile matching an implant to be inserted into the receiving channel.

In some embodiments, the cutting tool comprises a robotically controlled cutting tool operably connected to a remote computing device.

In some embodiments, the remote computing device is configured to control the cutting surface of the cutting tool as the cutting tool is moved through the cutting channel, thereby controlling cutting of the receiving channel.

In some embodiments, the baseplate further comprises at least one engagement feature configured to mate with at least one receptacle on the bone, thereby positioning the baseplate on the bone.

In some embodiments, the cutting comprises an internal shape configured to fit the engagement portion of the cutting tool.

In some embodiments, the baseplate is sized based upon the implant to be inserted into the receiving channel.

In some embodiments, the cut guide portion is sized to provide a receiving channel for a plurality of implant sizes.

In some embodiments, the bone comprises a tibia.

In some embodiments, the baseplate is configured to fit the first bone to be cut when a first side of the baseplate is positioned up and fit a second bone to be cut when a second side of the baseplate is positioned up.

There is also provided a method of preparing a bone to receive an implant. The method includes: determining, by a computing system, a keel depth profile for the implant; tracking, by the computing system, a cutting tool as the cutting tool moves in a cut guide; determining, by the computing system, a cut depth for each position of the cutting tool as the cutting tool moves in the cut guide; and operating, by the computing system, the cutting tool to cut a receiving channel in the bone as the cutting tool moves through the cut guide, the receiving channel corresponding in depth to the keel depth profile for the implant.

In some embodiments, operating the cutting tool comprises extending a cutting surface of the cutting tool to the determined cut depth for each position of the cutting tool as the cutting tool moves in the cut guide.

In some embodiments, the cutting surface comprises a cutting bur.

In some embodiments, the bone comprises a tibia.

The example embodiments as described above can provide various advantages over prior techniques. For example, more accurate channels for receiving an implant keel can be create using the devices and systems as described herein when compared to prior techniques. Such channels results in a tighter fit of the implant, which encourages better bone growth around the implant. The devices and systems described herein also provide safety advantages over prior techniques. For example, prior techniques including using punch tools to form a keel channel, can punch through the cancellous bone and potentially crack the cortical bone. The devices and systems as described herein eliminate such a risk.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

This disclosure is directed to example systems and methods of guiding a surgeon toward making an optimal channel or otherwise narrow cut in bone to prepare it for the receipt of an implant with a keel or other lengthy protrusion. In the following description, for purposes of explanation, numerous specific details are set forth in order to provide a thorough understanding of example embodiments. It will be evident to one skilled in the art, however, that embodiments can be practiced without these specific details.

For the purposes of this specification, the term "implant" is used to refer to a prosthetic device or structure manufactured to replace or enhance a biological structure. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

When a surgeon places a prosthetic implant in a joint, the surgeon often creates holes or channels in the bone that mirror protrusions on the implant. The interface between the holes or channels in the bone and the implant protrusions keep the implant affixed to the bone in the proper position.

For example, during a total knee arthroplasty (TKA), the surgeon can place one implant in the patient's tibia and a second implant in the patient's femur. Typically, a femoral implant has one or more posts that are designed to be inserted into the bone. To prepare the femur, the surgeon can cut relatively deep holes into the patient's femur into which a surgical adhesive and the implant posts are inserted. Conversely, due to the shape and size of the tibia, the tibial implant can have a keel having a specific depth and shape profile that ideally is fittingly inserted into the tibia to ensure proper fit and purchase. Generally, a tighter fit between the implant keel and the prepared tibia results in less adhesive being required to hold the implant in position and promotes better bone growth around the implant keel. However, current tools and instruments for making an accurate channel cut to receive a tibial implant keel or similar lengthy raised protrusion are ineffective and their use is time-consuming.

Figure 1:
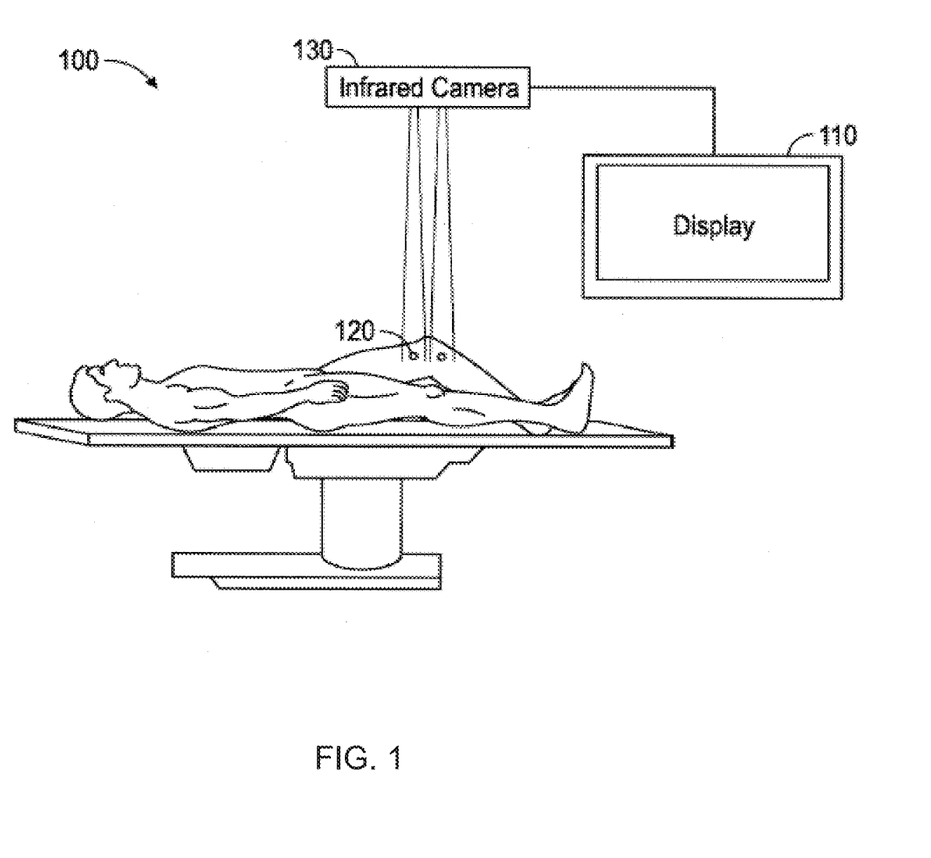
FIG. 1 illustrates a block diagram depicting a system for providing surgical navigation to ensure an orthopedic procedure is consistent with a surgical plan in accordance with certain embodiments of the present disclosure.

FIG. 1 is a block diagram depicting a system 100 for providing optical surgical navigation during a procedure through virtual placement of an implant, according to certain embodiments. A computer system 110 can provide a display for viewing data provided by optical trackers 120 and an infrared camera system 130. The optical trackers 120 and infrared camera system 130 can provide data relevant to the bones in, for example, a knee joint. In certain embodiments, the infrared camera system 130 can detect tracking spheres located on the optical trackers 120 in order to gather location data regarding the patient's femur and tibia on which a procedure is to be performed. As such, during a procedure such as a TKA, the computer system 110 can track the position of the bones and their relative position to each other throughout the procedure.

Figure 2:
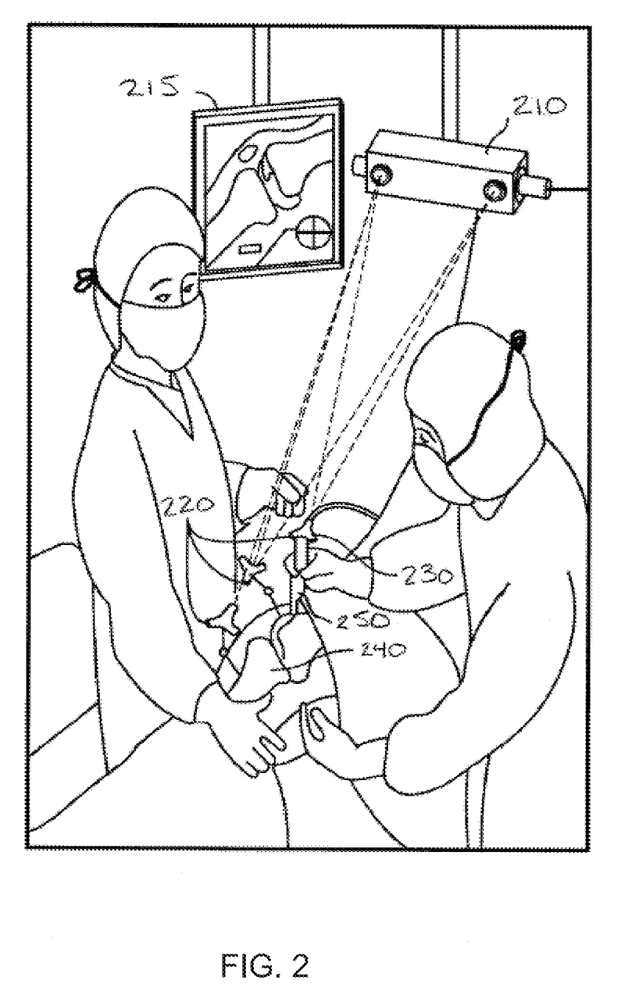
FIG. 2 depicts an illustration of an operating room with a system employing a cutting tool in accordance with certain embodiments of the present disclosure.

FIG. 2 illustrates an exemplary optical surgical navigation setup. The infrared camera 210 and optical trackers 230 can be used to perform surgical navigation in concert with, for example, computer system 110 as described above. The optical trackers 230 can be rigidly attached to any object 240 (such as the patient's femur or tibia) that the surgeon wishes to track during the procedure. The camera 210 can take continuous images of the workspace during the procedure and the markers 220 are detected from those images. Using the known rigid spatial relationship of the markers 220 on the image frame, the position of a tool 250 in a three-dimensional space can be determined and continuously output to the display 215. The display 215 can also continuously display the tool 250 location relative to the patient's anatomy.

Figure 3A:
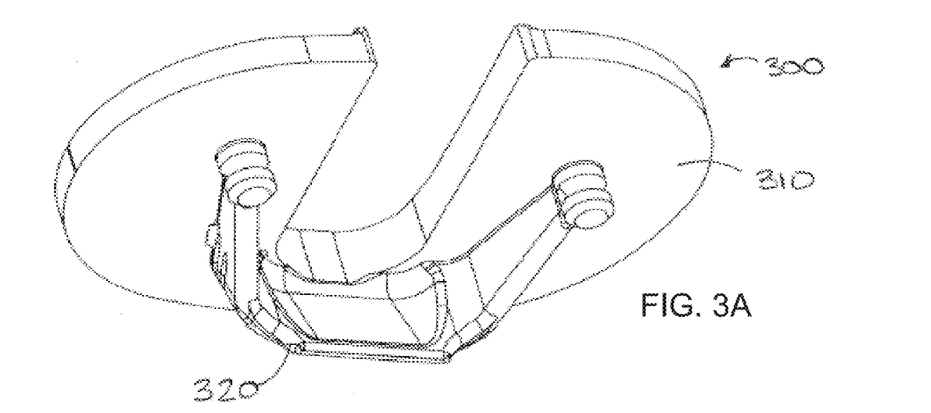
FIG. 3A depicts a perspective view of a tibial implant showing the keel to be inserted into a patient's bone in accordance with certain embodiments of the present disclosure.
Figure 3B:
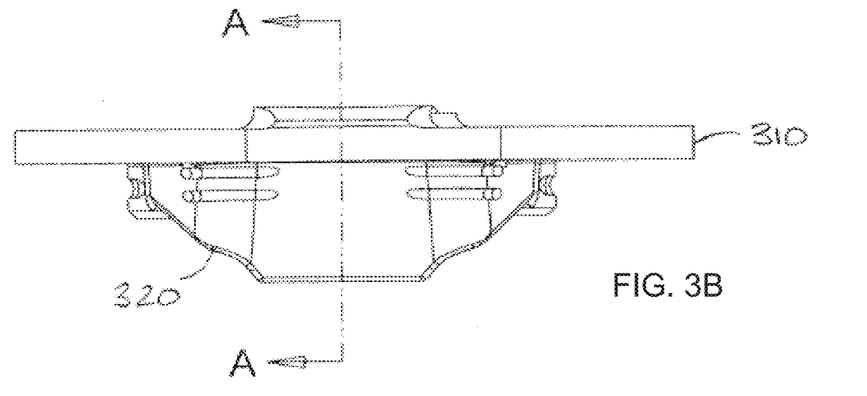
FIG. 3B depicts an elevational view of a tibial implant in accordance with certain embodiments of the present disclosure.
Figure 3C:
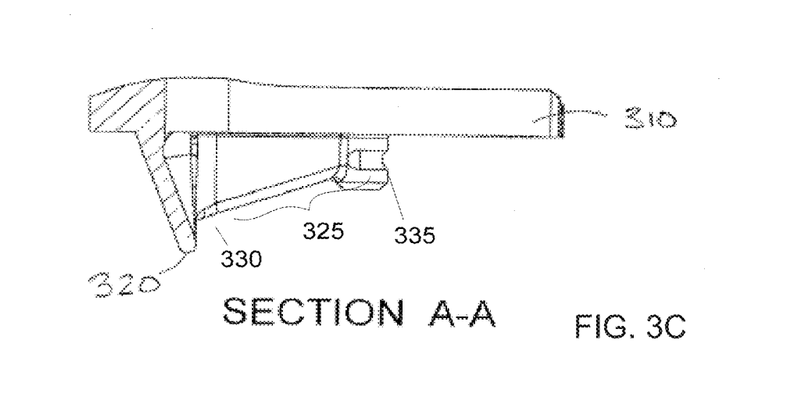
FIG. 3C depicts a cross-sectional view of a tibial implant along section A-A of FIG. 3B in accordance with certain embodiments of the present disclosure.

FIGS. 3A-3C illustrate various views of a sample embodiment of a tibial implant 300. The implant 300 may include a flat weight-bearing section 310 and keel 320. The keel 320 may have a complex geometry of varying depths and is designed to be embedded into the tibia to hold it in place.

In certain implementations, the keel 320 can have a complex depth profile that varies along the length of the keel. For example, as shown in FIG. 3C, illustrating a side view of the implant 300, the keel 320 has a specific depth profile 325. For example, at an anterior portion 330 of the depth profile 325, the keel 320 may have a different depth than at a posterior portion 335 of the depth profile. In some examples, the anterior portion 330 of the keel 320 can vary in depth from about 15.0 mm to about 20.0 mm. In some examples, the posterior portion 335 of the keel 320 can vary in depth from about 5.5 mm to about 8.0 mm.

In certain implementations, the geometry of the depth profile 325 can vary. For example, the keel can slope at a constant rate from the anterior portion 330 to the posterior portion 335. In some examples, as shown in FIG. 3C, the depth profile can drop quickly after the anterior portion 330, slope gradually up to the posterior portion 335, and then increase in depth again. It should be noted that the actual keel 320 geometry and depth profile 325 may be determined based upon what type and size of tibial implant is being used.

Figure 4A:
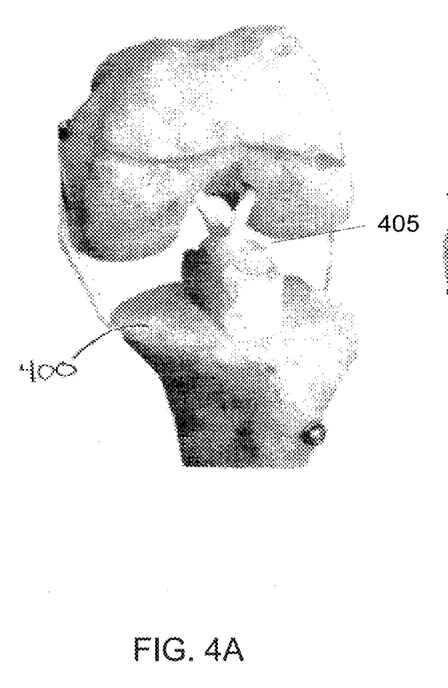
FIG. 4A depicts an illustration of a tibia prepared for creation of a keel channel in accordance with certain embodiments of the present disclosure.

FIG. 4A illustrates a mocked-up prepared tibia 400 prior to cutting for the keel 320. As shown in FIG. 4A, the tibia 400 can be prepared by cutting away a portion of the bone material. Depending upon the type of tibia implant being used, the shape of and type of cuts made on the tibia can vary accordingly. For example, as shown in FIG. 4A, the tibia 400 can be cut such that an island 405 of bone material is left, thereby preserving the anterior cruciate ligament (ACL) and the posterior cruciate ligament. Such a tibial cut can be used, for example, with an implant from the JOURNEY II XR implant family. JOURNEY II XR is a registered trademark of SMITH & NEPHEW of Memphis, Tenn. However, for other implant types, the tibia 400 can be prepared to accept those specific types of implants. Similarly, for different sized implants within the same implant family, the tibia can be appropriately prepared to receive and implant having a particular size.

Figure 4B:
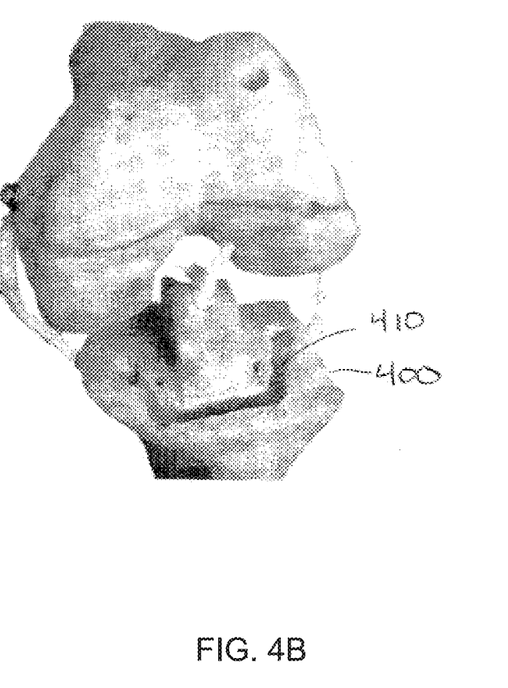
FIG. 4B depicts an illustration of a tibia with a keel channel cut into it in accordance with certain embodiments of the present disclosure.

FIG. 4B illustrates the tibia 400 with a keel channel 410 cut into it in a manner consistent with the present disclosure. As noted above, for a particular implant, the keel can have a specific depth profile. In certain implementations, the keel channel 410 can be created to mirror the depth profile of the implant to be inserted into the tibia, thereby resulting in a more secure and tight fit. In traditional approaches, a punch tool may be used to create the keel channel 410. Typically the punch tool is positioned on the patient's tibia and impacted using, for example, a snap hammer. The punch tool is then removed, leaving behind the keel channel 410. However, such an approach has various drawbacks. For example, various sized implants, even within the same implant family, can have different depth profiles. As such, a different punch tool may be required for each implant size. Additionally, depending upon the position of the punch tool, the punch tool could hit the harder cortical bone of the tibia, thereby causing a fracture or blowout of the bone.

The present disclosure teaches additional devices and techniques for creating the keel channel 410 for use with, for example, a tibial implant such as implant 300. The techniques include using a cut guide and a robotically controlled cutting tool to create a keel channel that has a depth profile specifically formed to match the tibial implant being used.

Figure 5:
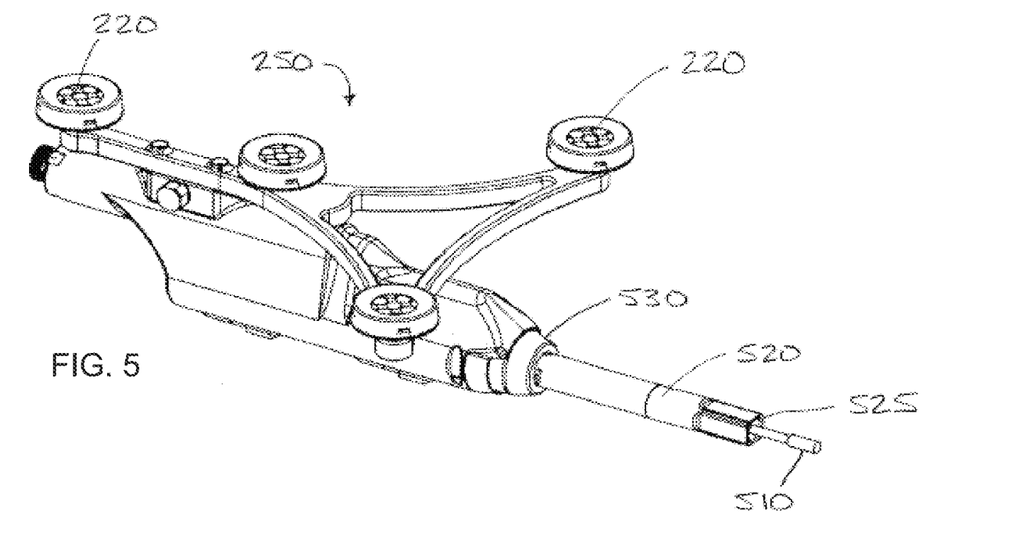
FIG. 5 depicts a perspective view of a hand-held cutting device with a cut guard in accordance with certain embodiments of the present disclosure.

For example, FIG. 5 illustrates a hand-held cutting tool 250 that can be used in conjunction with certain embodiments of the present invention. As disclosed in U.S. Pat. No. 6,757,582 to Brisson et at, the entirety of which is incorporated herein as if more fully set forth, the tool 250 is tracked by a camera 210 that optically detects the trackers 220 and communicates that information to a computer system that is also tracking the bones within the surgical space and comparing the location of the tool 250 with a pre-determined surgical plan. In certain embodiments, the tool 250 turns on when the bur 510 is in a position where the surgical plan indicates the bone should be cut and turns off when the tool 250 is near bone that is to be preserved. In certain other embodiments, the bur is caused to extend and cut in places where it is supposed to cut and retracts behind the cut guard 520 when it is not supposed to cut the bone. In still further embodiments, the bur 510 may be extended a controlled distance away from the cut guard 520 so that it only cuts to a certain depth or at a certain distance away from the distal end 525 of the cut guard in accordance with the surgical plan. Such robotically controlled features, in concert with the cut guard 520 and cutting guide as described below, can be used to accurately create a keel channel having a specific depth profile for a selected tibial implant.

Figure 6:
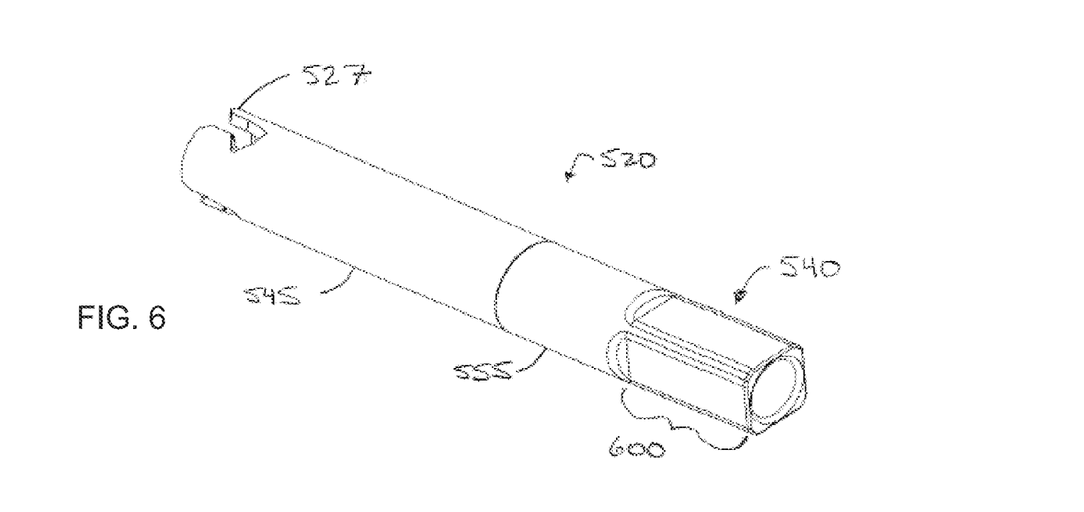
FIG. 6 depicts a perspective view of a cut guard in accordance with certain embodiments of the present disclosure.

FIG. 6 illustrates a cut guard 520 consistent with certain embodiments of the present invention. As illustrated in FIG. 5, the cut guard 520 is attached at its proximal end 527 to a distal end 530 of the cutting tool 250 via an attachment mechanism such as that disclosed in U.S. Patent Application Publication No. 2011/0262224 to McCandless et al., the entirety of which is incorporated herein as if more fully set forth. In certain other embodiments, a quick coupler or a similar coupling mechanism that releasably secures the cut guard 520 to the cutting tool 250 can be used. The cut guard 520 is tubular so that when it is attached to the cutting tool 250, the bur 510 can extend axially within it. In certain embodiments, the cut guard 520 can have an engagement portion 540 at its distal end 525 that has a length 600. In certain implementations, the engagement portion 540 can include a rounded square cross-sectional shape. It should be noted that a rounded square cross-sectional shape is shown by way of example only, and the engagement portion 540 can include other cross-sectional shapes as well. Those of skill in the art will note that other cross-sectional shapes could be used, such as cylindrical or rectangular for example. Regardless of shape, the engagement portion 540 can be configured to have two opposing parallel surfaces that work with a cutting guide, as more fully discussed in the next paragraph, to mechanically constrain the movement of the cutting tool 250.

Figure 7A:
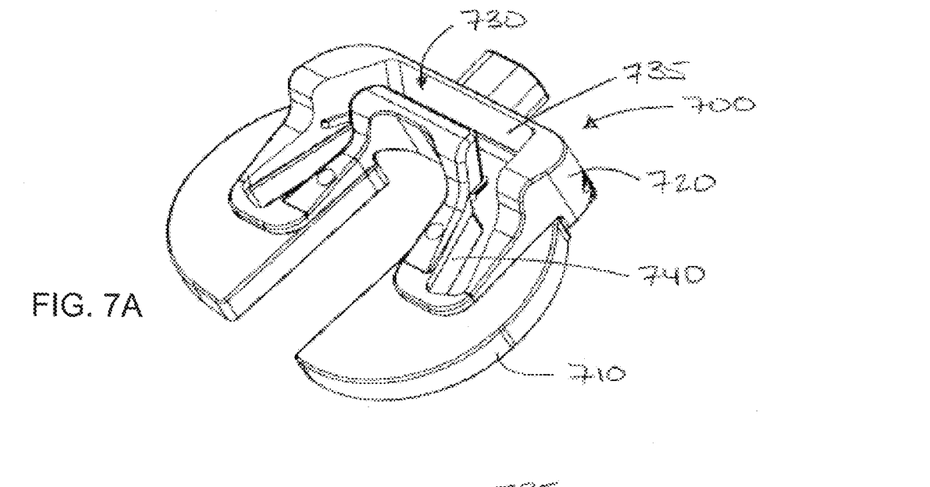
FIG. 7A depicts a perspective view of a cutting guide in accordance with certain embodiments of the present disclosure.
Figure 7B:
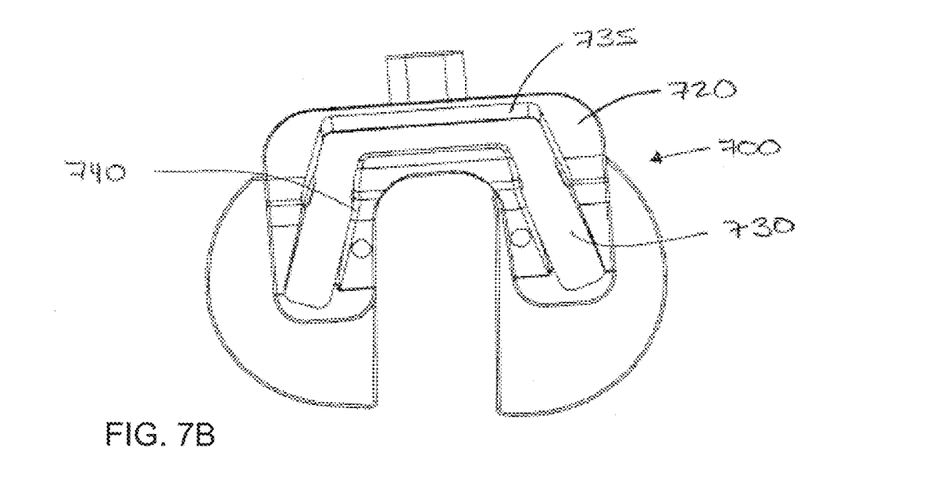
FIG. 7B depicts a plan view of a cutting guide in accordance with certain embodiments of the present disclosure.
Figure 7C:
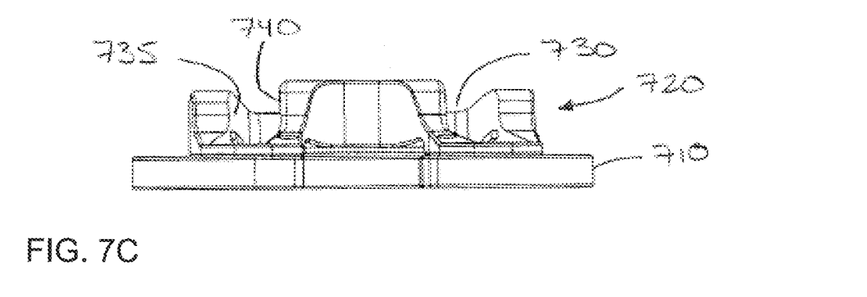
FIG. 7C depicts an elevational view of a cutting guide in accordance with certain embodiments of the present disclosure.

FIGS. 7A-C illustrate a cutting guide 700 that is fittingly matched to a total knee tibia implant 300 as set forth in FIGS. 3A-C and consistent with certain embodiments of the disclosed invention. The cutting guide can include a baseplate 710 that is intended to be securely disposed on the previously prepared tibia illustrated at FIG. 4A during a tibia preparation procedure. In some examples, the baseplate is configured such that it can be sized to a specific implant size. For example, in a specific implant family (such as the JOURNEY II XR family as described above), each implant size can have a corresponding baseplate 710. In some examples, the baseplate 710 can be configured to fit multiple sizes within a family. For example, implant sizes 1 and 2 can share a first baseplate, implant sizes 3 and 4 can share a second baseplate, and so on.

In certain implementations, the baseplate 710 can be reversible to accommodate both the left tibia implant and the right tibia implant. For example, when positioned with a first side up, the baseplate 710 can be sized and shaped to fit the right tibia. When flipped over and positioned with the second side up, the baseplate 710 can be sized and shaped to fit the left tibia. In some examples, the baseplate 710 can further include one or more divots, posts, or other engagement features for positioning the baseplate on the tibia. For example, when the tibia is prepared (e.g., as shown in FIG. 4A), one or more small holes can be drilled or otherwise cut into the cancellous bone material. These holes can correspond to, for example, divots or posts positioned on the baseplate 710 to ensure that the baseplate is properly positioned on the tibia and will not move when the keel channel is cut.

In certain embodiments, the cutting guide 700 can further include a guide portion 720. The guide portion 720 can be configured to removably attach to the baseplate 710. In some examples, the guide portion 720 can be configured to include a cutting channel 730 sized to receive at least a portion of the length 600 of the engagement portion 540 of the cut guard 520. For example, as noted above, the engagement portion 540 of the cut guard 520 can include a specific cross-sectional shape. The cutting channel 730 can be shaped to accept the cross-sectional shape of the engagement portion 540. In some examples, the engagement portion 540 can further include a keying feature that prevents the engagement portion from being improperly inserted into the cutting channel 730.

The cutting channel 730 can include an outer wall 735 and an inner wall 740 that form the cutting channel 730 and are positioned to slidingly receive the at least a portion of the length 600 of the cut guard 520. Together, the engagement portion 540 of the cut guard 520 and the inner and outer walls 735, 740 of the cutting channel 730 can mechanically constrain lateral and angular movement of the tool 250. For example, the lateral movement and angle of the bur 510 can be limited to a path and angle defined by the cutting channel 730. By constraining the position of the bur 510, the cut guard 520 can be used to form the keel channel 410 in the bone to match the keel 320 of a particular implant 300. Constraining the cut guard 520 in this way ensures the bone is prepared at the exact shape and angle required by the keel 320 and also that no native bone is unnecessarily removed. Preservation of native bone permits better outcomes by providing a stronger base for the implant while at the same time increasing the chances of a successful revision should that become necessary.

In certain embodiments, the cutting guide 700 can be separated into the baseplate 710 and the guide portion 720 so that the baseplate 710 can be used as a trial to determine the optimal size and orientation of the final implant. Then, when size and orientation are determined, the guide portion 720 can be securely and rigidly disposed on the baseplate 710 in preparation for creation of the keel channel.

Figure 8:
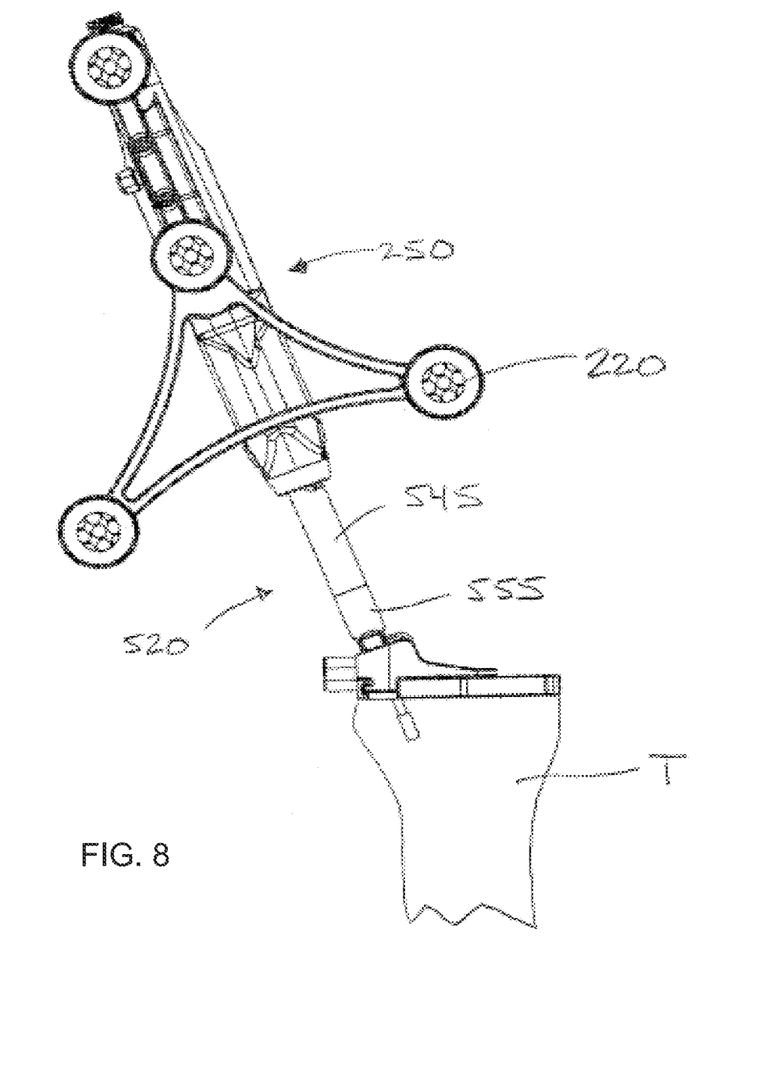
FIG. 8 depicts an illustration of a cutting tool cutting a channel in a tibia through the use of a cut guide in accordance with certain embodiments of the present disclosure.

FIG. 8 illustrates the use of the cutting tool 250 inserted into the cutting channel 730 to form the keel channel 410 in a patient's tibia, T. An example of a completed keel channel 410 is set forth at FIG. 4B.

While the cutting channel 730 constrains the movement of the bur 510 to a desired angle relative to the longitudinal axis of the bone and to a set path on the prepared surface of the bone 400, certain embodiments of the cutting guide 700 do not mechanically constrain the depth of the keel channel 410 even though the keel 320 has varied elevations. Instead, the distance that the bur 510 is extended is controlled by the cutting tool system by comparing the location of the bur with the surgical plan. In other embodiments, the depth of the keel channel 410 is controlled by stopping the bur 510 when the system detects that the cut is at the appropriate depth into the bone such that it is consistent with the surgical plan. Controlling the depth of the cut along the entirety of the cutting channel 730 further minimizes the amount of native bone removed in the procedure. Certain embodiments of this system are ideal for cuts of variable depth that have to be prepared along a prescribed line or curve, but those of skill in the art will recognize many other uses for this system.

In certain other embodiments, the bur 510 can be extended a fixed distance beyond the distal end 525 of the cutting guard guide 520. In some examples, a flange can be formed at the bottom of one or both of the channel walls 735, 740 so that the distal end of the cutting guard is mechanically constrained in terms of how deep it can go into the cutting channel 730. Such a design can mechanically constrain the depth of the bur in the patient's tibia.

Referring to FIGS. 6 and 8, in certain embodiments, the cut guard 520 can include a fixed section 545 and a rotatable section 555 that can axially rotate independently of the fixed section to enable the surgeon to rotate the tool 250 for comfort or to ensure the trackers 220 can be seen by the camera 210 while the engagement portion 540 remains engaged with the cut guide 700.

In certain embodiments, the cutting tool as disclosed herein can be used in accordance with the following method. A health care practitioner first applies a cutting guide to a bone that will receive an implant. The cutting guide has a channel for receiving an engagement portion of the cutting tool wherein the channel is shaped and oriented to match the keel of the implant. The health care practitioner next inserts the engagement portion of the cutting tool into the channel and begins to cut a keel channel into the bone in accordance with a previously determined surgical plan. As the cutting tool is moved along the entire path of the channel, the system described herein controls the depth of the cut so that it is consistent with the surgical plan. At the same time, the channel in the cutting guide constrains the lateral shape and angle of the cut into the bone. Once the keel channel has been completely cut, the cutting guide is removed and the implant is placed in the bone.

Figure 9:
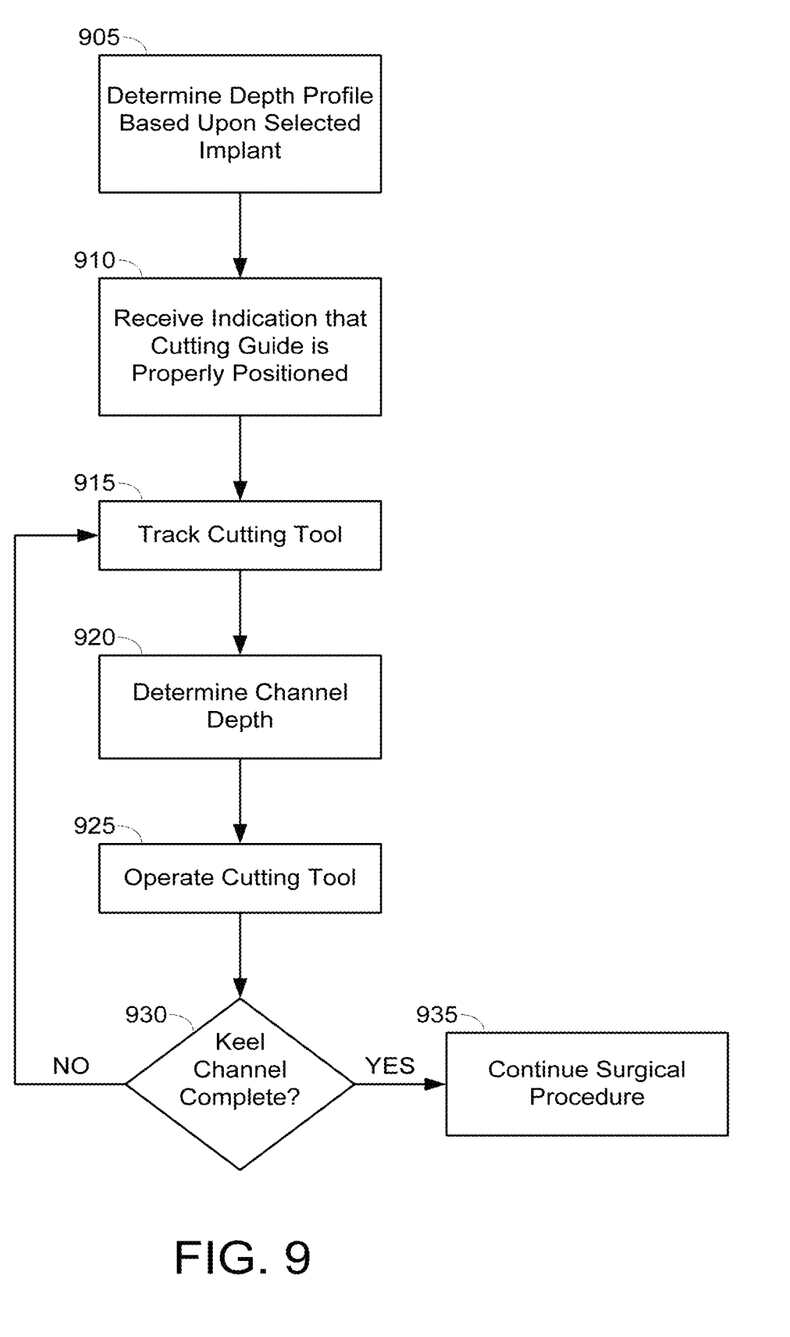
FIG. 9 depicts a sample process flow for using the cutting guide in accordance with certain embodiments of the present disclosure.

When cutting the keel channel, the depth of the channel itself may be controlled by a computer system integrated into a robotically assisted surgical system. For example, computer system 110 as described above can be further configured to provide operational signals to a rotary cutting tool. For example, the computer system 110 can determine the current position of the rotary tool in the cut guide, determine the depth of the keel channel for that specific position, and extend the cutting bur such that the channel is cut to the proper depth. FIG. 9 illustrates a sample process for using a computing system integrated into a robotically assisted surgical system to provide a keel channel having a depth profile that accurately matches and mirrors a depth profile for an implant to be placed into the keel channel.

As shown in FIG. 9, the computing system can determine 905 a depth profile for a keel channel based upon a selected implant. For example, as noted above, the selected implant may be chosen from the JOURNEY II XR implant family and have a specific keel size and depth profile. Based upon this information, the computing system can determine 905 the depth profile for the implant keel. The computing system also may receive 910 an indication that the cutting guide is properly positioned on, for example, a patient's right tibia. This indication can be received 910 from a physician inputting the information into, for example, a display or another similar input device operably connected to the computing system.

The computing system can track 915 the cutting tool using a navigation system and optical markers such as those described herein. Based upon the position of the cutting tool, the computing system can determine 920 the channel depth for that particular position. For example, if the cutting tool is positioned at an anterior portion of the keel channel, the computing system may determine that the channel depth for that particular position is about 18 mm. The computing system can operate 925 the cutting tool appropriately according to the current position. To continue the previous example, the computing system may operate 925 the cutting tool by activating the cutting bur and extending the cutting bur to 18 mm. The physician can then slide the cutting tool through the cutting guide in a similar process as noted above. As the cutting tool moves, the computing system can determine 930 whether the keel channel is complete. If the computing system does determine 930 that the keel channel is complete, the computing system can continue 935 the surgical procedure as planned. In the computing system determines 930 that the keel channel is not complete, the computing system can continue to track 915 the cutting tool, determine 920 the keel channel depth for an updated position of the cutting tool, and operate 925 the cutting tool accordingly.

It should be noted that, in addition to automatically operating the cutting tool to create a depth profile to match a selected implant, the computing system can also determine the overall size of the keel channel. For example, as shown in FIG. 4B, the keel channel may have a U shape positioned around island 410. Depending upon the size of the implant being used, each arm of the U shape can be a different length. For example, for a larger implant size, the keel channel may extend further toward the posterior portion of the tibia. Conversely, for a smaller implant size, the posterior channel length may be reduced. In such an example, a single cut guide can be used that accommodates the longer channel cuts. However, to prepare a keel channel for the smaller implant size, the computing system can alter the cutting operation of the cutting device to prepare the shorter keel channel that does not extend as far toward the posterior portion of the tibia. Thus, the cut guide as described herein, along with a robotically assisted cutting device, can be used to accommodate implants having different depth profiles as well as implants having different keel channel lengths.

It should also be noted that tibia preparation and keel channel cutting as described herein is provided by way of example only. The techniques, systems, and devices as described herein can be applied to any implant preparation where a keel channel may be created in a bone for receiving an implant.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of preparing a bone of a patient to receive an implant, the method comprising:

determining, by a computing system, a keel depth profile for the implant;

aligning, by the computing system, a cutting guide with respect to the bone, wherein the cutting guide comprises:

a cutting channel having an internal u-shaped configuration configured to receive at least a first portion of a cutting tool, and guide the first portion of the cutting tool to cut a receiving channel in the bone to be cut, wherein the receiving channel comprises a depth profile matching the keel depth profile of the implant to be inserted into the receiving channel, wherein the cutting guide is sized based upon the implant to be inserted into the receiving channel;

a surface in which the cutting channel is located, the surface configured to guide a second portion of the cutting tool when the first portion of the cutting tool is located in the cutting channel; and a baseplate;

aligning, by the computing system, the cutting guide with respect to the bone to be cut when a first side of the baseplate is positioned up facing away from the bone; and aligning, by the computing system, the cutting guide with respect to a second bone to be cut when a second side of the baseplate, opposite to the first side of the baseplate, is positioned up facing away from the second bone, wherein the second bone is anatomically opposite to the first bone with respect to a sagittal plane of the patient; and guiding, by the computing system, the cutting tool, through the aligned cutting guide, to cut the receiving channel in the bone or the second bone to which the cutting guide is aligned, wherein at least a portion of the surface of the cutting guide is non-planar with respect to another portion of the surface of the cutting guide, such that an angular position of the first portion of the cutting tool received in the cutting channel is altered as the second portion of the cutting tool moves along the surface of the cutting guide.

2. The method claim 1, wherein the bone comprises a tibia.

3. The method of claim 1, wherein the cutting guide is configured to be coupled to a robotic arm, wherein aligning the cutting guide with respect to the bone comprises positioning, by the computing system, the robotic arm to align the cutting guide with respect to the bone.

4. The method of claim 1, wherein the cutting guide is sized to provide the receiving channel for a plurality of implant sizes.

\* \* \* \* \*